(12) United States Patent
Seong et al.

(10) Patent No.: US 8,834,892 B2
(45) Date of Patent: Sep. 16, 2014

(54) METHOD OF PREPARING LIVE VIRAL VACCINES BY GENETIC ENGINEERING OF VIRAL GENOME

(75) Inventors: Baik Lin Seong, Seoul (KR); Yo Han Jang, Goyang-si (KR); Kwang Hee Lee, Goyang-si (KR); Young Ho Byun, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 187 days.

(21) Appl. No.: 13/214,634

(22) Filed: Aug. 22, 2011

(65) Prior Publication Data

US 2012/0171243 A1 Jul. 5, 2012

(30) Foreign Application Priority Data

Dec. 31, 2010 (KR) ........................ 10-2010-0139734

(51) Int. Cl.
*A61K 39/145* (2006.01)
*A61K 39/12* (2006.01)
*C12N 7/00* (2006.01)

(52) U.S. Cl.
CPC ..... *A61K 39/145* (2013.01); *C12N 2760/16134* (2013.01); *C07K 2319/50* (2013.01); *C12N 2760/16122* (2013.01); *C12N 2760/16162* (2013.01); *C12N 7/00* (2013.01)
USPC .................. 424/206.1; 424/204.1; 424/209.1

(58) Field of Classification Search
CPC ........... C12Q 1/6883; A61K 47/48215; A61K 47/48323; A61K 2039/55561; A61K 39/145; C12N 2760/16122; C07K 14/81; C07K 14/005; C07K 2319/50
See application file for complete search history.

(56) References Cited

FOREIGN PATENT DOCUMENTS

| KR | 10-2010-0045436 A | 5/2010 |
|---|---|---|
| KR | 1020110113615 A | 10/2011 |
| WO | 2004-111249 A2 | 12/2004 |

OTHER PUBLICATIONS

Palker et al., Protective efficacy of intranasal cold-adapted influenza A/New Caledonia/20/99 (H1N1) vaccines comprised of egg-or cell culture-derived reassortants, 2004, Virus Research, vol. 105, pp. 183-194.*
Yoshimori, A. et al., "A novel method for evaluation and screening of caspase inhibitory peptides by the amino acid positional fitness score", BMC Pharmacology, 4: 7 (May 22, 2004).
Korean Office Action for Korean Application No. 10-2010-0139734, dated Sep. 25, 2012.

* cited by examiner

*Primary Examiner* — Benjamin P Blumel
(74) *Attorney, Agent, or Firm* — Edwards Wildman Palmer LLP; Kongsik Kim

(57) ABSTRACT

Disclosed is an attenuation method of an influenza virus, that is, a reassortant virus and a preparation method thereof. The disclosed reassortant virus has, in a ratio of 6:2, genes encoding a recombinant non-toxic protein and a wild type non-toxic protein, and genes encoding toxic proteins, HA (hemagglutinin) and NA (neuraminidase), of an influenza virus, the recombinant non-toxic protein consisting of a substituted caspase recognition sequence without a change of a protein size within the wild type non-toxic protein of the influenza virus. The disclosed attenuated influenza virus shows a high attenuation without a reduction of productivity in a fertilized egg. Accordingly, the method can be used as an economically efficient live vaccine preparation method which has both safety and efficiency and can use a fertilized egg as a production system. Also, since a protein is not removed or modified during attenuation, the method can be used in combination with a conventional attenuated vaccine preparation technology such as cold-adaptation.

4 Claims, 8 Drawing Sheets

FIG. 5

SEQUENCE LISTING

<160> NUMBER OF SEQ ID NOS: 17

<210> SEQ ID NO 1
<211> LENGTH: 716
<212> TYPE: PRT
<213> ORGANISM: Influenza A virus

<400> SEQUENCE: 1

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
```

```
            115                 120                 125
Ile Tyr Tyr Leu Glu Lys Ala Asn Lys Ile Lys Ser Glu Lys Thr His
130                 135                 140
Ile His Ile Phe Ser Phe Thr Gly Glu Glu Met Ala Thr Lys Ala Asp
145                 150                 155                 160
Tyr Thr Leu Asp Glu Glu Ser Arg Ala Arg Ile Lys Thr Arg Leu Phe
                    165                 170                 175
Thr Ile Arg Gln Glu Met Ala Ser Arg Gly Leu Trp Asp Ser Phe Arg
                180                 185                 190
Gln Ser Glu Arg Gly Glu Glu Thr Ile Glu Glu Arg Phe Glu Ile Thr
            195                 200                 205
Gly Thr Met Arg Lys Leu Ala Asp Gln Ser Leu Pro Pro Asn Phe Ser
210                 215                 220
Ser Leu Glu Asn Phe Arg Ala Tyr Val Asp Gly Phe Glu Pro Asn Gly
225                 230                 235                 240
Tyr Ile Glu Gly Lys Leu Ser Gln Met Ser Lys Glu Val Asn Ala Arg
                245                 250                 255
Ile Glu Pro Phe Leu Lys Thr Thr Pro Arg Pro Leu Arg Leu Pro Asn
                260                 265                 270
Gly Pro Pro Cys Ser Gln Arg Ser Lys Phe Leu Leu Met Asp Ala Leu
            275                 280                 285
Lys Leu Ser Ile Glu Asp Pro Ser His Glu Gly Glu Gly Ile Pro Leu
290                 295                 300
Tyr Asp Ala Ile Lys Cys Met Arg Thr Phe Phe Gly Trp Lys Glu Pro
305                 310                 315                 320
Asn Val Val Lys Pro His Glu Lys Gly Ile Asn Pro Asn Tyr Leu Leu
                325                 330                 335
Ser Trp Lys Gln Val Leu Ala Glu Leu Gln Asp Ile Glu Asn Glu Glu
                340                 345                 350
Lys Ile Pro Lys Thr Lys Asn Met Lys Lys Thr Ser Gln Leu Lys Trp
            355                 360                 365
Ala Leu Gly Glu Asn Met Ala Pro Glu Lys Val Asp Phe Asp Asp Cys
370                 375                 380
Lys Asp Val Gly Asp Leu Lys Gln Tyr Asp Ser Asp Glu Pro Glu Leu
385                 390                 395                 400
Arg Ser Leu Ala Ser Trp Ile Gln Asn Glu Phe Asn Lys Ala Cys Glu
                405                 410                 415
Leu Thr Asp Ser Ser Trp Ile Glu Leu Asp Glu Ile Gly Glu Asp Val
                420                 425                 430
Ala Pro Ile Glu His Ile Ala Ser Met Arg Arg Asn Tyr Phe Thr Ser
            435                 440                 445
Glu Val Ser His Cys Arg Ala Thr Glu Tyr Ile Met Lys Gly Val Tyr
            450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
                500                 505                 510
Asn Asp Thr Asp Val Val Asn Phe Val Ser Met Glu Phe Ser Leu Thr
            515                 520                 525
Asp Pro Arg Leu Glu Pro His Lys Trp Glu Lys Tyr Cys Val Leu Glu
530                 535                 540
```

```
Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715

<210> SEQ ID NO 2
<211> LENGTH: 757
<212> TYPE: PRT
<213> ORGANISM: Influenza A virus

<400> SEQUENCE: 2

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
```

-continued

```
            195                 200                 205
Lys Gln Arg Leu Asn Lys Arg Ser Tyr Leu Ile Arg Ala Leu Thr Leu
        210                 215                 220
Asn Thr Met Thr Lys Asp Ala Glu Arg Gly Lys Leu Lys Arg Arg Thr
225                 230                 235                 240
Ile Ala Thr Pro Gly Met Gln Ile Arg Gly Phe Val Tyr Phe Val Glu
            245                 250                 255
Thr Leu Ala Arg Ser Ile Cys Glu Lys Leu Glu Gln Ser Gly Leu Pro
        260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
        290                 295                 300
Asp Asn Thr Lys Trp Asn Glu Asn Gln Asn Pro Arg Met Phe Leu Ala
305                 310                 315                 320
Met Ile Thr Tyr Met Thr Arg Asn Gln Pro Glu Trp Phe Arg Asn Val
            325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
        355                 360                 365
Pro Ala Glu Met Leu Ala Ser Ile Asp Leu Lys Tyr Phe Asn Asp Ser
370                 375                 380
Thr Arg Lys Lys Ile Glu Lys Ile Arg Pro Leu Leu Ile Glu Gly Thr
385                 390                 395                 400
Ala Ser Leu Ser Pro Gly Met Met Gly Met Phe Asn Met Leu Ser
            405                 410                 415
Thr Val Leu Gly Val Ser Ile Leu Asn Leu Gly Gln Lys Arg Tyr Thr
            420                 425                 430
Lys Thr Thr Tyr Trp Trp Asp Gly Leu Gln Ser Ser Asp Asp Phe Ala
        435                 440                 445
Leu Ile Val Asn Ala Pro Asn His Glu Gly Ile Gln Ala Gly Val Asp
        450                 455                 460
Arg Phe Tyr Arg Thr Cys Lys Leu Leu Gly Ile Asn Met Ser Lys Lys
465                 470                 475                 480
Lys Ser Tyr Ile Asn Arg Thr Gly Thr Phe Glu Phe Thr Ser Phe Phe
            485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
        515                 520                 525
Val Ile Lys Asn Asn Met Ile Asn Asn Asp Leu Gly Pro Ala Thr Ala
        530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Ile
            565                 570                 575
Lys Lys Leu Trp Glu Gln Thr Arg Ser Lys Ala Gly Leu Leu Val Ser
        580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Gln Gly Arg Leu
        610                 615                 620
```

```
Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                    645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
690             695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
            755

<210> SEQ ID NO 3
<211> LENGTH: 759
<212> TYPE: PRT
<213> ORGANISM: Influenza A virus

<400> SEQUENCE: 3

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Thr
50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val Gln Tyr Pro
                100                 105                 110

Lys Ile Tyr Lys Thr Tyr Phe Glu Arg Val Glu Arg Leu Lys His Gly
            115                 120                 125

Thr Phe Gly Pro Val His Phe Arg Asn Gln Val Lys Ile Arg Arg Arg
130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
210                 215                 220

Ser Ser Val Tyr Ile Glu Val Leu His Leu Thr Gln Gly Thr Cys Trp
```

```
            225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
                260                 265                 270

Ser Ala Asp Pro Leu Ala Ser Leu Leu Glu Met Cys His Ser Thr Gln
                275                 280                 285

Ile Gly Gly Ile Arg Met Val Asp Ile Leu Arg Gln Asn Pro Thr Glu
                290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
                340                 345                 350

Lys Ile Arg Val His Glu Gly Tyr Glu Glu Phe Thr Met Val Gly Arg
                355                 360                 365

Arg Ala Thr Ala Ile Leu Arg Lys Ala Thr Arg Leu Ile Gln Leu
                370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
                420                 425                 430

Gln Leu Leu Arg His Phe Gln Lys Asp Ala Lys Val Leu Phe Gln Asn
                435                 440                 445

Trp Gly Val Glu Pro Ile Asp Asn Val Met Gly Met Ile Gly Ile Leu
                450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val
                485                 490                 495

Ser Ile Asp Arg Phe Leu Arg Ile Arg Asp Gln Arg Gly Asn Val Leu
                500                 505                 510

Leu Ser Pro Glu Glu Val Ser Glu Thr Gln Gly Thr Glu Lys Leu Thr
                515                 520                 525

Ile Thr Tyr Ser Ser Ser Met Met Trp Glu Ile Asn Gly Pro Glu Ser
                530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ser Arg Gly Gln Tyr
                580                 585                 590

Ser Gly Phe Val Arg Thr Leu Phe Gln Gln Met Arg Asp Val Leu Gly
                595                 600                 605

Thr Phe Asp Thr Ala Gln Ile Ile Lys Leu Leu Pro Phe Ala Ala Ala
                610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655
```

```
Asn Tyr Asn Lys Ala Thr Lys Arg Leu Thr Val Leu Gly Lys Asp Ala
                660                 665                 670

Gly Thr Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Lys Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 4
<211> LENGTH: 498
<212> TYPE: PRT
<213> ORGANISM: Influenza A virus

<400> SEQUENCE: 4

Met Ala Ser Gln Gly Thr Lys Arg Ser Tyr Glu Gln Met Glu Thr Asp
1               5                   10                  15

Gly Gly Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Met Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
```

```
                   260                 265                 270
Lys Ser Cys Leu Pro Ala Cys Val Tyr Gly Pro Ala Val Ala Ser Gly
            275                 280                 285
Tyr Asp Phe Glu Arg Glu Gly Tyr Ser Leu Val Gly Ile Asp Pro Phe
        290                 295                 300
Arg Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Leu Ser Phe Ile Lys Gly Thr Lys Val
            340                 345                 350
Leu Pro Arg Gly Lys Leu Ser Thr Arg Gly Val Gln Ile Ala Ser Asn
        355                 360                 365
Glu Asn Met Glu Thr Met Glu Ser Ser Thr Leu Glu Leu Arg Ser Arg
    370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Ile Gln Pro Thr Phe Ser Val Gln Arg
                405                 410                 415
Asn Leu Pro Phe Asp Arg Thr Thr Ile Met Ala Ala Phe Asn Gly Asn
            420                 425                 430
Thr Glu Gly Arg Thr Ser Asp Met Arg Thr Glu Ile Ile Arg Met Met
        435                 440                 445
Glu Ser Ala Arg Pro Glu Asp Val Ser Phe Gln Gly Arg Gly Val Phe
    450                 455                 460
Glu Leu Ser Asp Glu Lys Ala Ala Ser Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn

<210> SEQ ID NO 5
<211> LENGTH: 252
<212> TYPE: PRT
<213> ORGANISM: Influenza A virus

<400> SEQUENCE: 5

Met Ser Leu Leu Thr Glu Val Glu Thr Tyr Val Leu Ser Ile Ile Pro
1               5                   10                  15
Ser Gly Pro Leu Lys Ala Glu Ile Ala Gln Arg Leu Glu Asp Val Phe
            20                  25                  30
Ala Gly Lys Asn Thr Asp Leu Glu Val Leu Met Glu Trp Leu Lys Thr
        35                  40                  45
Arg Pro Ile Leu Ser Pro Leu Thr Lys Gly Ile Leu Gly Phe Val Phe
    50                  55                  60
Thr Leu Thr Val Pro Ser Glu Arg Gly Leu Gln Arg Arg Arg Phe Val
65                  70                  75                  80
Gln Asn Ala Leu Asn Gly Asn Gly Asp Pro Asn Asn Met Asp Lys Ala
                85                  90                  95
Val Lys Leu Tyr Arg Lys Leu Lys Arg Glu Ile Thr Phe His Gly Ala
            100                 105                 110
Lys Glu Ile Ser Leu Ser Tyr Ser Ala Gly Ala Leu Ala Ser Cys Met
        115                 120                 125
Gly Leu Ile Tyr Asn Arg Met Gly Thr Val Thr Thr Glu Val Ala Phe
```

```
                130                 135                 140
Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 6
<211> LENGTH: 97
<212> TYPE: PRT
<213> ORGANISM: Influenza A virus

<400> SEQUENCE: 6

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
                20                  25                  30

Ile Gly Ile Leu His Leu Thr Leu Trp Ile Leu Asp Arg Leu Phe Phe
            35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 7
<211> LENGTH: 230
<212> TYPE: PRT
<213> ORGANISM: Influenza A virus

<400> SEQUENCE: 7

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
                20                  25                  30

Leu Asp Arg Leu Arg Arg Asp Gln Lys Ser Leu Arg Gly Arg Gly Ser
            35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Leu Ser Arg Asp Trp Ser Met Leu Ile Pro Lys Gln Lys Val Ala
                100                 105                 110
```

```
Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 8
<211> LENGTH: 121
<212> TYPE: PRT
<213> ORGANISM: Influenza A virus

<400> SEQUENCE: 8

Met Asp Pro Asn Thr Val Ser Ser Phe Gln Asp Ile Leu Leu Arg Met
1               5                   10                  15

Ser Lys Met Gln Leu Glu Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Ile Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120

<210> SEQ ID NO 9
<211> LENGTH: 566
<212> TYPE: PRT
<213> ORGANISM: Influenza A virus

<400> SEQUENCE: 9

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80
```

```
Thr Leu Ile Asp Ala Leu Leu Gly Asp Pro His Cys Asp Val Phe Gln
                85                  90                  95

Lys Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
130                 135                 140

Gly Val Thr Gln Asn Gly Gly Ser Ile Ala Cys Lys Arg Gly Pro Asp
145                 150                 155                 160

Ser Gly Phe Phe Ser Arg Leu Asn Trp Leu Thr Lys Ser Glu Ser Thr
                165                 170                 175

Tyr Pro Val Leu Asn Val Thr Met Pro Asn Asn Asp Asn Phe Asp Lys
            180                 185                 190

Leu Tyr Ile Trp Gly Ile His His Pro Ser Thr Asn Gln Glu Gln Thr
        195                 200                 205

Ser Leu Tyr Val Gln Ala Ser Gly Arg Val Thr Val Ser Thr Arg Arg
210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495
```

```
Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Thr Cys Gln Arg Gly Asn Ile
545                 550                 555                 560

Arg Cys Asn Ile Cys Ile
                565

<210> SEQ ID NO 10
<211> LENGTH: 385
<212> TYPE: PRT
<213> ORGANISM: Influenza A virus

<400> SEQUENCE: 10

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Val Thr Thr
            20                  25                  30

Val Thr Leu His Phe Lys Gln Tyr Glu Cys Asp Ser Pro Ala Ser Asn
            35                  40                  45

Gln Val Met Pro Cys Glu Pro Ile Ile Ile Glu Arg Asn Ile Thr Glu
        50                  55                  60

Ile Val Tyr Leu Asn Asn Thr Thr Ile Glu Lys Glu Ile Cys Pro Lys
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp His Gly Lys
            115                 120                 125

Cys Tyr Gln Phe Ala Leu Gly Gln Gly Thr Thr Leu Asp Asn Lys His
            130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asp
            195                 200                 205

Gly Arg Leu Val Asp Ser Ile Gly Ser Trp Ser Gln Asn Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Glu Ile Val His Ile Ser Pro Leu Ser Gly Ser Ala
            260                 265                 270

Gln His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
            290                 295                 300
```

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
            325                 330                 335

Cys Arg Asn Pro Asn Asn Glu Arg Gly Asn Gln Gly Val Lys Gly Trp
            340                 345                 350

Ala Phe Asp Asn Gly Asp Asp Val Trp Met Gly Arg Thr Ile Ser Lys
            355                 360                 365

Asp Leu Arg Ser Gly Tyr Glu Thr Phe Lys Val Leu Val Val Gly Pro
            370                 375                 380

Thr
385

<210> SEQ ID NO 11
<211> LENGTH: 4
<212> TYPE: PRT
<213> ORGANISM: Artificial Sequence
<220> FEATURE:
<223> OTHER INFORMATION: Caspase recognition sequence

<400> SEQUENCE: 11

Asp Glu Val Asp
1

<210> SEQ ID NO 12
<211> LENGTH: 4
<212> TYPE: PRT
<213> ORGANISM: Artificial Sequence
<220> FEATURE:
<223> OTHER INFORMATION: Caspase recognition sequence

<400> SEQUENCE: 12

Ala Glu Val Asp
1

<210> SEQ ID NO 13
<211> LENGTH: 4
<212> TYPE: PRT
<213> ORGANISM: Artificial Sequence
<220> FEATURE:
<223> OTHER INFORMATION: Caspase recognition sequence

<400> SEQUENCE: 13

Ile Glu Thr Asp
1

<210> SEQ ID NO 14
<211> LENGTH: 4
<212> TYPE: PRT
<213> ORGANISM: Artificial Sequence
<220> FEATURE:
<223> OTHER INFORMATION: Caspase recognition sequence

<400> SEQUENCE: 14

Trp Glu His Asp
1

<210> SEQ ID NO 15
<211> LENGTH: 4
<212> TYPE: PRT
<213> ORGANISM: Artificial Sequence
<220> FEATURE:
<223> OTHER INFORMATION: Caspase recognition sequence

```
<400> SEQUENCE: 15

Tyr Val Ala Asp
1

<210> SEQ ID NO 16
<211> LENGTH: 11
<212> TYPE: PRT
<213> ORGANISM: Artificial Sequence
<220> FEATURE:
<223> OTHER INFORMATION: Upstream Polybasic Clevage Site of HA gene

<400> SEQUENCE: 16

Pro Gln Arg Glu Ser Arg Arg Lys Lys Arg Gly
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Downstream Polybasic Clevage Site of HA gene

<400> SEQUENCE: 17

Pro Gln Arg Glu Lys Arg Gly
1               5
```

METHOD OF PREPARING LIVE VIRAL VACCINES BY GENETIC ENGINEERING OF VIRAL GENOME

CROSS-REFERENCE TO RELATED APPLICATION

This application claims under 35 U.S.C. §119(a) the benefit of Korean Application No. 10-2010-0139734 filed Dec. 31, 2010, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 10, 2014, is named 89159-301264.txt and is 39,731 bytes in size.

TECHNICAL FIELD

The present invention relates to a method for attenuating influenza virus

BACKGROUND ART

Influenza viruses in the form of a flu epidemic or a pandemic occurring every year threaten human health. As the most efficient method for preventing this, a vaccine is used. Vaccines are divided into two types, an inactivated vaccine using a surface protein of a virus as an antigen, and a live vaccine with an attenuated virus. In live vaccine preparation methods developed up to now, a cold adapted attenuated live vaccine has been mainly used as a prevention vaccine (Watanabe, S. et al., Influenza A Virus Lacking M2 Protein as a Live Attenuated Vaccine. *J Virol* 83, 5947-5950 (2009); Steel, J. et al., Live Attenuated Influenza Viruses Containing NS1 Truncations as Vaccine Candidates against H5N1 Highly Pathogenic Avian Influenza. *J Virol* 83, 1742-1753 (2009); Perez, J. T. et al., MicroRNA-mediated species-specific attenuation of influenza A virus. *Nat Biotech* 27, 572-576 (2009); Stech, J. et al., A new approach to an influenza live vaccine: modification of the cleavage site of hemagglutinin. *Nat Med* 11, 683-689 (2005)). However, live vaccines have safety problems, and thus their use for infants, old people, or some people with a reduced immunity level is restricted (Cox, R. J. et al., Influenza Virus: Immunity and Vaccination Strategies. Comparison of the Immune Response to Inactivated and Live, Attenuated Influenza Vaccines. *Scandinavian Journal of Immunology* 59, 1-15 (2004)).

As a method for improving the safety of a live vaccine, there has been recently suggested a method of employing two or more attenuation methods in one kind of live vaccine. As a conventional technology, there is a method for introducing a cold-adaptation character into a virus, thereby resulting in propagation inhibition at a regular human body temperature of 36 to 37° C. (Monto, A. S. et al., Evaluation of an attenuated, cold-recombinant influenza B virus vaccine. *J Infect Dis* 145, 57-64 (1982); Lee, K.-H. et al., Characterization of live influenza vaccine donor strain derived from cold-adaptation of X-31 virus. *Vaccine* 24, 1966-1974 (2006); Belshe, R. B. et al., Current status of live attenuated influenza virus vaccine in the US. *Virus Research* 103, 177-185 (2004); Seo, S.-U. et al., Development and characterization of a live attenuated influenza B virus vaccine candidate. *Vaccine* 26, 874-881 (2008)). As another conventional technology, there is a method for attenuating a virus by removing or modifying a nonstructural protein 1 (NS1) from among influenza virus proteins. Also, there has been developed a method for attenuating a virus by removing M2 ion channel protein, and modifying hemagglutinin (HA) and a protein cleavage site, Further, there has been recently developed a method for reducing gene replication efficiency of a virus within a cell by using a gene silencing mechanism of miRNA.

Meanwhile, virus attenuation often even causes the destruction of propagation capability of a virus in a fertilized egg. Accordingly, in preparation of an attenuated live vaccine, sometimes, it is required to change a preparation system from a fertilized egg to a cell line (such as a MDCK cell line or a Vero cell line). Also, in some cases, an expensive enzyme required for virus propagation has to be added to a cell culture fluid.

Meanwhile, the inventors of the present invention developed X-31 ca as a donor strain of a cold-adapted attenuated live vaccine, which has a strong immunogenicity and a high propagation capability at a replication-competent temperature, and has a high attenuation at a non-replication-competent temperature (Lee, K.-H. et al., Characterization of live influenza vaccine donor strain derived from cold-adaptation of X-31 virus. *Vaccine* 24, 1966-1974 (2006)). The X-31 ca virus can be replicated in a lung and an upper airway of a mouse through infection ($10^4$ PFU) in spite of its high attenuation character. The infection with a live vaccine in a host cell is apparently directly related to the immunogenicity. However, a long-term survival of a virus in an infected host cell may cause a toxic problem such as spontaneous genetic variation and the virus' reassortment together with another human virus (Cox, R. J., Brokstad, K. A. & Ogra, P. Influenza Virus: Immunity and Vaccination Strategies. Comparison of the Immune Response to Inactivated and Live, Attenuated Influenza Vaccines. *Scandinavian Journal of Immunology* 59, 1-15 (2004)).

Accordingly, in order to eliminate a live vaccine's latent risk raised from the conventional technology and previous research, the inventors of the present invention have tried to develop an attenuation method which can more quickly remove a virus from a virus-infected cell, and can improve stability of a live vaccine without damage to immunogenicity and high productivity, and then thus have completed this invention.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

An object of the present invention is to provide a method for attenuating an influenza virus.

Also, another object of the present invention is to provide a method for more quickly removing an influenza virus from an infected cell.

A further object of the present invention is to provide an attenuated virus which can be quickly removed from an infected cell and has a high immunogenicity and a high productivity in a fertilized egg.

A yet further object of the present invention is to provide a method for vaccinating a host by using an attenuated virus which can be quickly removed from an infected cell and has a high immunogenicity and a high productivity in a fertilized egg.

A yet further object of the present invention is to provide a method for preparing a recombinant virus and preparing an attenuated live vaccine, in which the virus is prepared by any one selected from the group consisting of measles virus, mumps virus, rubella virus, poliovirus, common cold virus, rotavirus, yellow fever virus, varicella virus, hepatitis B virus, human papillomavirus, HSV-1, HSV-2, adenovirus and coxsackie virus.

In order to achieve the above objects, the inventors of the present invention completed the present invention by introducing a protease recognition site into a protein within an influenza virus, and using a host's self-defense mechanism in virus attenuation.

The inventors of the present invention noticed that caspase (protease) activated in an influenza virus-infected cell cleaves matrix proteins, resulting in apoptosis of the infected cell. Then, they prepared, as an influenza virus protein, a recombinant protein in which an amino acid residue to be cleaved by caspase is introduced. They found that in a cell infected with a virus having the inventive recombinant protein, the virus's recombinant protein was cleaved by caspase and thus virus toxicity was significantly reduced. Also, the inventive attenuated virus induced the production of a large amount of antibodies in serum and a respiratory organ's mucosal tissue of a mouse. Also, it was observed that the attenuated virus having the inventive recombinant protein can maintain its high propagation capability in a fertilized egg used for mass production of a conventional live vaccine. Accordingly, the preparation of the inventive attenuated virus can employ a conventional live vaccine virus preparation process as it is, and thus is highly advantageous in view of economic efficiency due to there being no increase in an additional production cost. As described above, the present invention is characterized in that through recombination of various proteins within an influenza virus, the virus is subjected to an action of a host's defense mechanism. Thus, unlike the conventional technology, there is no need to remove or modify a specific protein. Accordingly, the present invention in combination with the conventional technology may be used for preparing a live vaccine using an attenuated virus. In this case, according to the characteristics of the conventional technology to be used in combination with the present invention, by adjusting the protein to be cleaved, the number of cleavage sites, etc., it is possible to secure balance of the immunogenicity and the safety of a live vaccine. Especially, in a case of a protease, since the activity is highly sensitive to a temperature, it is possible to inhibit the activity of the enzyme within a fertilized egg by changing a culture temperature of the fertilized egg. This allows a new type of attenuation method to be developed which can keep a live vaccine's productivity as it is.

An attenuated live vaccine has a very similar mechanism to an actual infection mechanism of a virus. It has a higher defense capability than an inactivated vaccine so that it can induce not only a specific antibody response but also a cell immune response. Accordingly, for attenuation of a developed live vaccine through cold-adaptation or subculture in a non-human cell, genetic mutation causing attenuation of a virus was randomly induced, and then, an attenuated virus barely showing any toxicity in a human cell was prepared and used as a live vaccine. However, with the development of molecular virology and the advent of reverse genetic technology, a live vaccine has been recently prepared by directly causing mutation in measles virus, mumps virus, rubella virus, poliovirus, common cold virus, rotavirus, yellow fever virus, varicella virus, hepatitis B virus, human papillomavirus, HSV-1, HSV-2, adenovirus and coxsackie virus (Lauring, A. S., Jones, J. O. & Andino, R. Rationalizing the development of live attenuated virus vaccines. Nat Biotech 28, 573-579 (2010)).

BRIEF DESCRIPTION OF THE DRAWINGS

The foregoing and other objects, features and advantages of the present invention will become more apparent from the following detailed description when taken in conjunction with the accompanying drawings in which:

FIG. 1 shows preparation of an influenza virus attenuated by caspase, in which FIG. 1a shows a schematic view illustrating introduction of a caspase recognition site into NP and NS1 proteins of an A/PR/8/34 virus, FIG. 1b shows the gene configurations of mutant viruses, FIG. 1c shows the western blot results of NP and NS1 protein expressions in MDCK cell lines infected with a wild type virus and mutant viruses, and FIG. 1d shows the results of NP and NS1 protein expressions after treatment of Z-DEVD-FMK as a caspase 3 inhibitor;

FIG. 2 shows an in vitro attenuation characteristic of a mutant virus, and a productivity of the mutant virus in a fertilized egg, in which FIG. 2a shows a propagation speed of the virus in an MDCK cell line under various temperature conditions, FIG. 2b shows a productivity of the virus in a fertilized egg under various temperature conditions, and FIG. 2c shows a comparison of a productivity reduction between a mutant virus and a WT virus in an MDCK cell line and a fertilized egg at respective temperatures, wherein each value is expressed as a log difference between the mutant virus and the WT virus in a maximum value in a MDCK cell line, and an average in a fertilized egg;

FIG. 3 shows the result of a toxicity test on a mouse model of a mutant virus, in which 6 mice in each group were infected with a wild type virus and mutant viruses, and for 2 weeks, weight and a death rate were observed, in which FIGS. 3a to 3d show weight changes after infection of a wild type virus, NP-C, NS1-C, and DM-C, respectively, and FIGS. 3e and 3f show measurement results of a propagation capability of a virus in a mouse, wherein the left graph shows a result in the lung, and the right graph shows a result in the upper airway fluid, and also FIGS. 3e and 3f show the results of a wild type virus and a DM-C virus, respectively, wherein on each marked date, after cervical dislocation, the mouse was dissected and the lung and the upper airway fluid were collected and mixed with PBS;

FIGS. 4a to 4d show a serum HI titer, a serum IgG titer, an upper airway fluid IgA titer, and a BAL IgA titer, respectively, and FIG. 4e shows a change in the weight of the mouse after infection of a wild type virus; and FIG. 5 shows attenuation, immunogenicity, and protectiveness of DM-C:H5N1 (a 6:2 reassortant virus of an H5N1), in which FIG. 5a shows a comparison between DM-C and DM-C:H5N1 in the propagation speed in an MDCK cell line, FIG. 5b shows a change in the weight of a mouse after inoculation of DM-C:H5N1, FIGS. 5c and 5d show the measurement results of an antibody response in an inoculated mouse (FIG. 5c: serum HI antibody titer, and FIG. 5d: serum IgG antibody titer), FIG. 5e shows a change in the weight of the mouse after infection of A/Aquatic bird/Korea/W81/05 (ma81) virus 10 $LD_{50}$ after 4 weeks from inoculation, and FIG. 5f shows the measurement results of a removal speed of an infection virus from a vaccine-inoculated mouse, in the lung and the upper airway fluid, respectively, wherein in the lung (left) and the upper airway fluid (right), the amount of infection virus was measured by using a MDCK cell line through TCID50.

DETAILED DESCRIPTION OF THE DISCLOSURE

Figure 1:
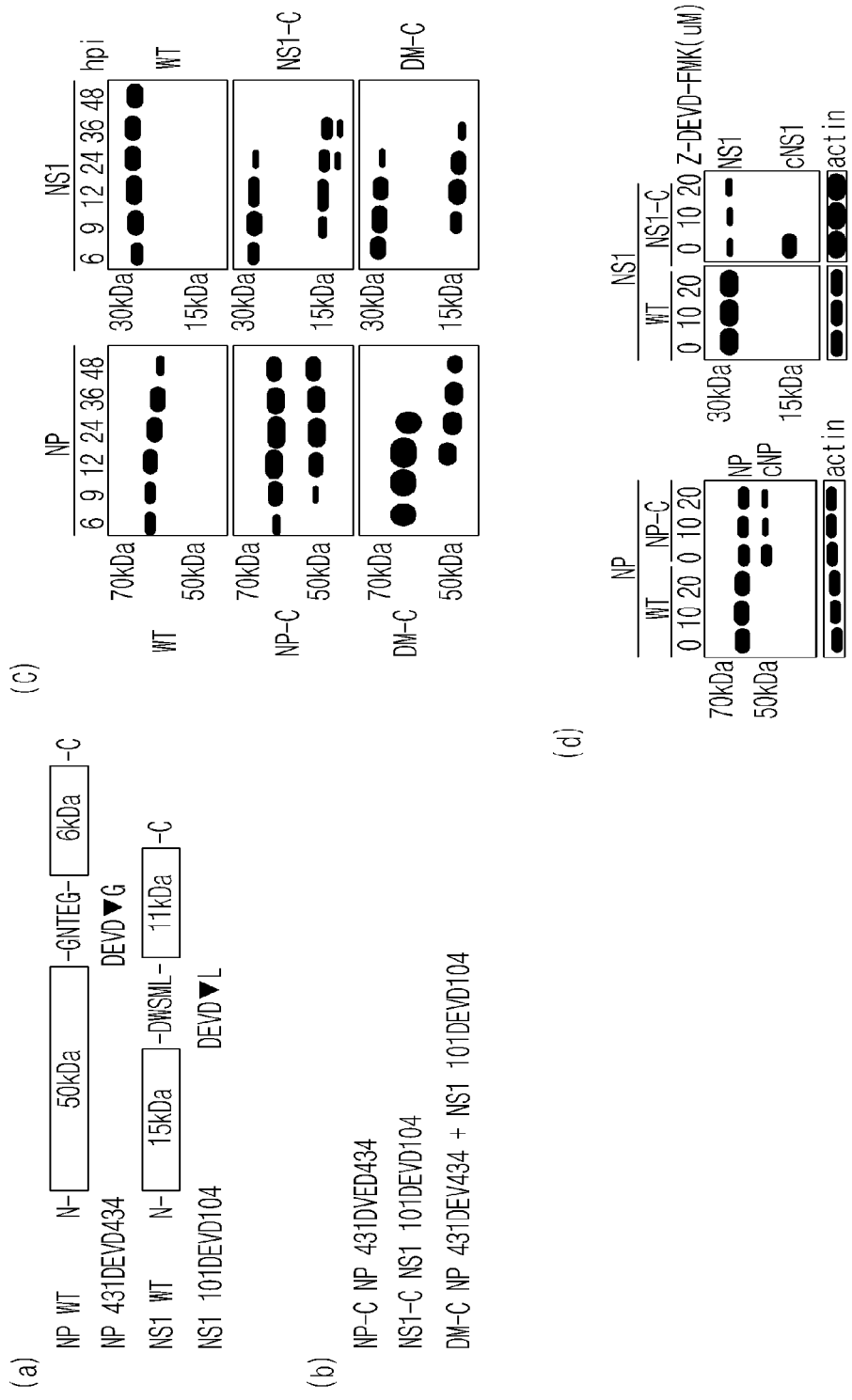

Hereinafter, the present invention will be described in more detail.

In the present invention, first, from among 11 proteins encoded by influenza virus, NP (nucleocapsid protein) and NS1 (nonstructural protein) were converted into substrates of a caspase. With several references on three-dimensional structures of the NP protein and the NS1 protein, a position was determined, into which a caspase recognition site can be introduced while the structural modification of these proteins and the productivity reduction in a fertilized egg are minimized (Ye, Q. et al., The mechanism by which influenza A virus nucleoprotein forms oligomers and binds RNA, Nature 444, 1078-1082, (2006); Boulo, S. et al., Nuclear traffic of influenza virus proteins and ribonucleoprotein complexes, *Virus Research* 124, 12-21, (2007); Bornholdt, Z. A. et al X-ray structure of influenza virus NS1 effector domain. *Nat Struct Mol Biol* 13, 559-560, (2006)). The caspase is divided into three sub groups according to a substrate specificity (Nicholson, D. W. Caspase structure, proteolytic substrates, and function during apoptotic cell death. *Cell Death Differ* 6, 1028-1042, (1999)). In order to effectively deliver an influenza virus protein, a DEVD amino acid sequence (SEQ ID NO: 11), which is a recognition sequence of caspase 3, 7 included in group II, was selected. Through a mutagenesis method using PCR, a DEVD (Asp-Glu-Val-Asp; SEQ ID NO: 11) sequence was inserted into the NP protein and the NS1 protein.

An NP-C virus including a DEVD (SEQ ID NO: 11) sequence inserted into an NP protein, an NS1-C virus including a DEVD sequence inserted into an NS1 protein, and a DM-C virus including a DEVD sequence inserted into both of an NP protein and an NS1 protein were prepared, and these viruses were used for experiments. Specifically, by using a reverse genetics technology, mutant viruses, that is, an NP-C virus, an NS1-C virus, and a DM-C virus, which have DEVD recognition sites at $431^{st}$ to $434^{th}$ positions from NP protein's amino terminal end of a human influenza A/PR/8/34 (H1N1) virus (ATCC No. VR-95), and at $101^{st}$ to $104^{th}$ positions from NS1 protein's amino terminal end were prepared (Hoffmann, E., Neumann, G., Kawaoka, Y., Hobom, G. & Webster, R. G. A DNA transfection system for generation of influenza A virus from eight plasmids. *Proceedings of the National Academy of Sciences of the United States of America* 97, 6108-6113 (2000)). Also, a DM-C:H5N1 6:2 reassortant virus was prepared by mixing genes of HA (GenBank accession EU146622), and NA (GenBank accession EU146623) of A/Indonesia/5/2005 (H5N1) virus with 6 genes within a DM-C virus. In an MDCK cell line (ATCC No. CCL-34) infected with the attenuated virus, after 9 hours from infection, cleavage of NP and NS1 proteins was observed. Then, with the lapse of time, the amount of cleaved proteins was increased, and became more than that of the original protein. This supports the fact that the cleavage by caspase is continuously carried out during apoptosis.

According to the present invention, it was determined that in proportion to the number of proteins converted into substrates of caspase, the attenuation level is increased. For example, a DM-C virus (an attenuated virus), which was prepared in such a manner that it has two caspase recognition sites, showed a attenuation character appropriate as a live vaccine in both in vitro and in vivo, and showed a high immunogenicity and a high protectiveness. When the DM-C virus was inoculated with a high concentration of $10^6$ PFU into a mouse, it was found that the virus was restrictively propagated. After 1 day from the inoculation, in the lung, the amount of virus was rapidly reduced up to $\frac{1}{100}$ of the inoculation amount, and in the upper airway fluid, for 10 days since the inoculation, no remaining virus was detected. After the infection of cells by an influenza virus, a caspase activated during apoptosis continuously cleaves its substrate proteins until apoptosis of the cells is completed. This vigorous activity allows a DM-C virus protein to be efficiently cleaved, thereby resulting in a rapid reduction of virus. Also, according to results from a recent piece of research, an NS1 protein has an apoptosis inhibiting function, and such a function is inhibited through cleavage by a caspase at the initial stage of infection. This facilitates an apoptosis process, thereby further facilitating the cleavage of NP and NS1. Such a process facilitates the cleavage of proteins of a recombinant virus and a reassortant virus, resulting in a significant decrease of a propagation speed of the viruses. A recombinant virus having a recognition site for any one protein of NP and NS1 proteins, unlike a DM-C virus, showed a lower toxicity than a wild type virus. However, the recombinant virus, when inoculated with a high concentration, resulted in reduction of a mouse weight.

For the attenuated virus according to the present invention, its propagation capability in a fertilized egg was observed. The inventive attenuated virus showed a slightly reduced productivity in a fertilized egg. It is assumed that such a result was caused by the occurring of cleavage of a virus protein in a fertilized egg with caspase activity, or a slight obstruction of a protein's natural structure and function due to the introduction of a caspase recognition site. However, when the culture temperature in a fertilized egg was lowered to 33° C., viruses were propagated up to $10^8$ PFU or more. Thus, there was hardly any difference in productivity between the wild type virus and the inventive attenuated virus. Although the relationship between the culture temperature and the virus productivity in a fertilized egg needs to be examined through detailed research, such a result provided an interesting possibility which allows a fertilized egg itself to be utilized as a production system.

An amino acid sequence of a protein used in the present invention is indicated with sequence Nos 1 to 10: RNA polymerase PA (SEQ ID NO.: 1), RNA polymerase PB1 (SEQ ID NO.: 2, RNA polymerase PB2 (SEQ ID NO.: 3), nucleocapsid protein (NP, SEQ ID NO.: 4), Matrix protein (M) (M1(matrix): SEQ ID NO.: 5, M2 (ion channel): SEQ ID NO.: 6), nonstructural protein (NS) (NS1: SEQ ID NO.: 7, NS2: SEQ ID NO.: 8), HA (hemagglutinin, SEQ ID NO.: 9) and NA (neuraminidase, SEQ ID NO.: 10).

The term "target protein" used in the present invention indicates a protein within an influenza virus, which is subjected to the action of a host enzyme.

The term "attenuated virus" used in the present invention is used jointly with "mutant virus".

In the present invention, as a protease, a caspase was used. However, it is natural that various enzymes may be used for the object of the present invention. Also, besides NP, NS1, and matrix proteins, membrane proteins such as HA, NA, and M2, or RNA polymerase such as PB2, PB1 and PA may be used as a target protein for the object of the present invention.

The term "caspase recognition sequence" used in the present invention indicates a sequence to be recognized and decomposed by caspase, and includes, but not limited to, DEVD (SEQ ID NO: 11), AEVD (SEQ ID NO: 12), IETD (SEQ ID NO: 13), WEHD (SEQ ID NO: 14), and YVAD (SEQ ID NO: 15; BMC Pharmacology 2004, 4:7, 2004 May, p 8 and Nature, Vol 437|6 Oct. 2005).

The term "influenza virus" used in the present invention indicates a virus which can cause influenza, and includes, but is not limited to, A type, B type, and C type influenza viruses.

The term "wild type non-toxic protein" used in the present invention indicates another protein except for surface proteins causing toxicity in a host, such as hemagglutinin (HA) and neuraminidase (NA), and includes, but is not limited to, three RNA polymerases PA, PB1 and PB2, nucleocapsid protein (NP), Matrix protein (M) and nonstructural protein (NS).

The term "recombinant non-toxic protein" used in the present invention indicates the wild type non-toxic protein substituted with a caspase recognition sequence.

The term "toxic protein surface protein" used in the present invention indicates a surface protein causing toxicity in a host, and includes, but is not limited to, hemagglutinin (HA) and neuraminidase (NA).

All references cited herein are incorporated herein by reference.

All animal experiments in the present invention were approved by Institutional Animal Care and Use Committee (IACUC) of Yonsei Laboratory Animal Research Center (YLARC), and carried out under YLARC IACUC guidelines.

As described above, the influenza virus including the inventive recombinant virus shows a high attenuation characteristic, and does not cause a reduction in productivity in a fertilized egg. Accordingly, the present invention may be developed as an economically efficient live vaccine preparation method which has both safety and efficiency and can use a fertilized egg as a production system. Also, since a protein is not removed or modified during attenuation, the present invention may be used in combination with a conventional attenuated vaccine preparation technology such as cold-adaptation.

EXAMPLES

Hereinafter, the present invention will be described in more detail with reference to Examples and Experimental Examples. However, Preparation Examples and Examples as described below are only for illustrative purposes and are not intended to limit the scope of the invention.

Example 1

Preparation of an Influenza Virus Attenuated by Caspase

By using a reverse genetic technology, mutant viruses, that is, an NP-C virus and an NS1-C virus, were prepared which have DEVD (SEQ ID NO: 11) recognition sites at 431st to 434th positions from NP protein's amino terminal end of a A/PR/8/34 virus, and at 101st to 104th positions from NS1 protein's amino terminal end (see FIGS. 1a and 1b) (Hoffmann, E., Neumann, G., Kawaoka, Y., Hobom, G. & Webster, R. G. A DNA transfection system for generation of influenza A virus from eight plasmids. Proceedings of the National Academy of Sciences of the United States of America 97, 6108-6113 (2000)). Also, a double mutant virus DM-C which has recognition sites for both NP and NS1 was prepared. Lipofectamine™ (Invitrogen) was used under the protocol of the manufacturer. The cDNA plasmid of 8 genes of an influenza virus, in an amount of 300 ng, was transfected into human embryonic kidney cell 293T cell line (HEK293T) (ATCC No. CRL-1573), and then after 48 hours, a supernatant was collected. It was determined whether a virus was produced in an MDCK cell line (ATCC No. CCL-34), through plaque assay. The supernatant, in which virus production was found, was inoculated into a fertilized egg (aged 11 days) and cultured. An allantoic fluid (albumen) of the fertilized egg cultured for 3 days was collected and the exact titer of the virus was measured through plaque assay. Also, a DM-C:H5N1 6:2 reassortant virus was prepared by mixing genes HA (hemagglutinin) and NA (neuraminidase) of an H5N1 (A/Indonesia/5/2005) virus with cDNA plasmid of other 6 genes of DM-C virus.

In order to secure the safety of the recombinant virus, a polybasic cleavage site of the HA gene was modified into a monobasic cleavage site (PQRESRRKKRG→PQREKRG; SEQ ID NOs: 16 and 17). In NP and NS1 genes of all of the prepared viruses, sequencing of cDNA obtained through RT-PCR was carried out so as to determine if there exists an undesired mutant.

In order to find the cleavage by caspase in the MDCK cell line, after infection of virus of 1 MOI (see FIG. 1(c)), cells were collected hourly and subjected to western blot. In the western blot, a polyclonal antibody against NP and NS1 proteins of A/WSN/33 (H1N1) virus (ATCC no. VR-219) prepared from a rabbit was used. As a secondary antibody, a goat anti-rabbit IgG monoclonal antibody (Sigma) conjugated with horseradish peroxidase was used with a dilution of 1:10,000. As a result, it was found that both NP 431DEVD434 and NS1 101DEVD104 proteins were cleaved in NP-C and DM-C (see FIG. 1c). After 24 hours from the treatment with Z-DEVD-FMK (BD Biosciences Material Number 550378) as a caspase 3 inhibitor, apoptotic cells were collected and subjected to western blot. As a result, it was found that cleavage was reduced. Thus, it was determined that the cleavage was caused by caspase (see FIG. 1d).

Example 2

Analysis on Propagation Capability in a Cell Line, by Caspase Cleavage

Figure 2:
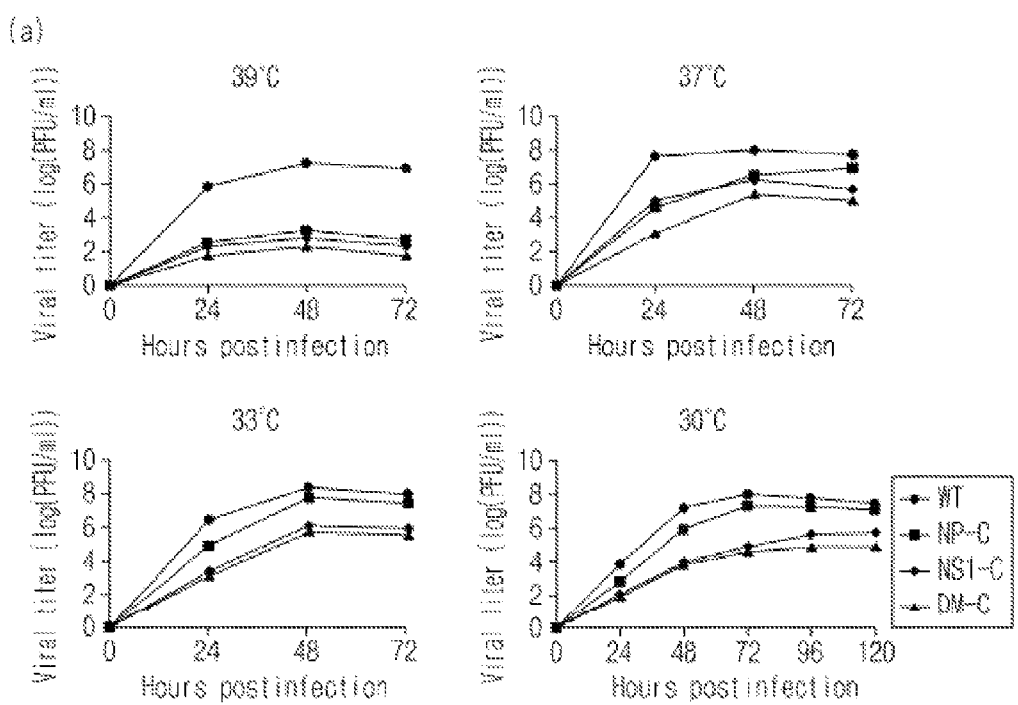
Figure 2:
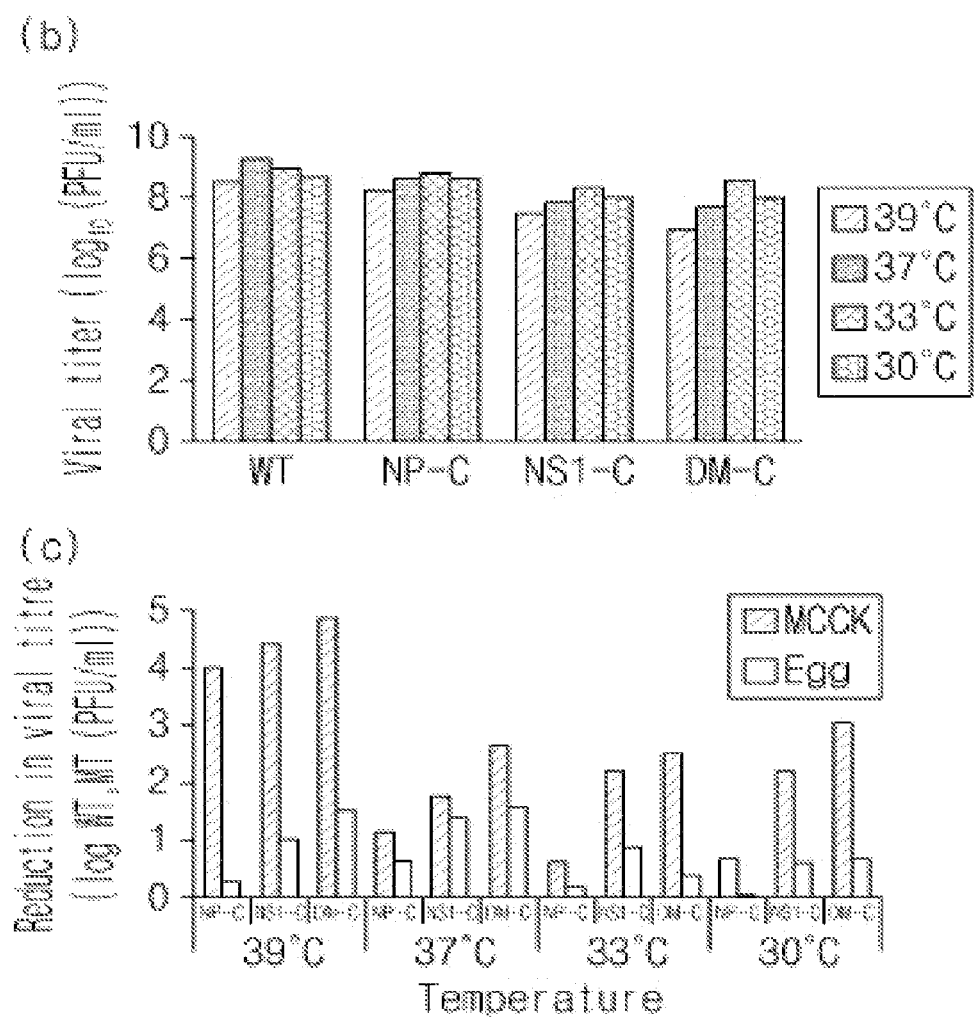
Figure 3:
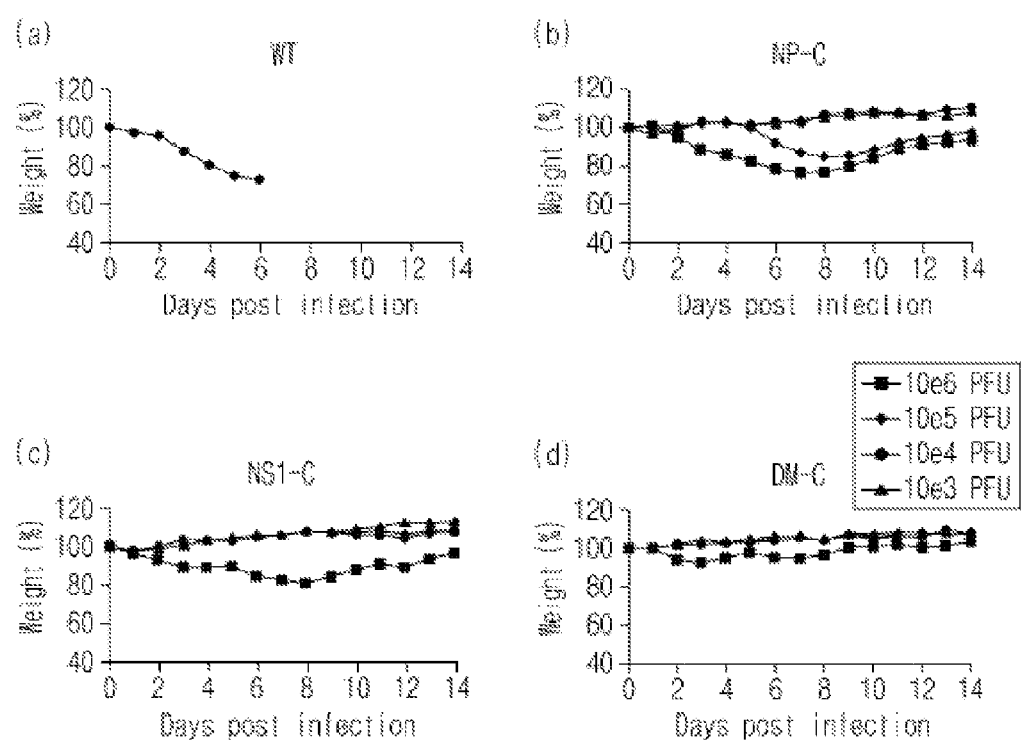
Figure 3:
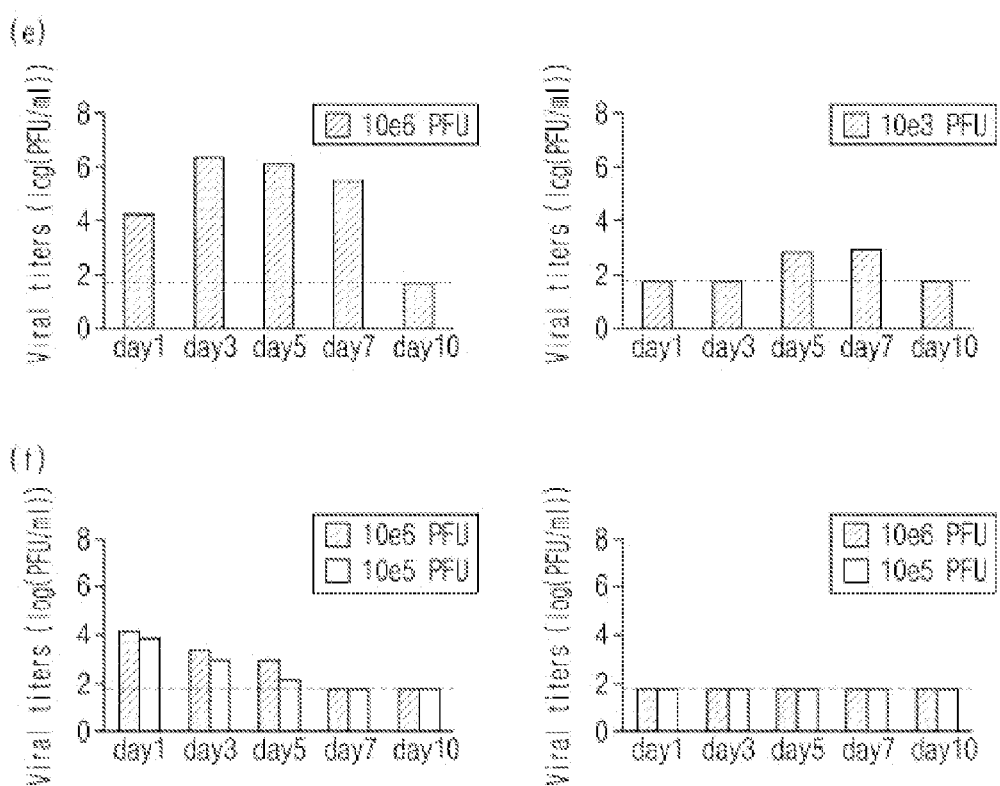

The attenuation character, in vitro, was determined. In order to determine the temperature's effect on virus propagation, a virus propagation speed in an MDCK cell line was measured under various temperature conditions. FIG. 2a shows the result. In order to measure the virus propagation speed according to temperatures, the MDCK cell line was infected with each virus of 0.001 MOI, and the supernatant was collected at an interval of 24 hours. Then, the virus titer in the supernatant was measured through plaque assay in the MDCK cell line. An average value from three experiments was obtained. Under all temperature conditions applied to the experiments, the propagation capability of a mutant virus was reduced, compared to that of a wild type virus. Especially, the propagation speed of the DM-C virus was further reduced compared to those of the NP-C virus or the NS1-C virus. From this result, it can be found that the introduction of caspase cleavage sites into two kinds of proteins further increased the extent of attenuation. Also, compared to the results at other temperatures, the propagation capability of the mutant virus was significantly reduced at a high temperature of 39° C. From this result, it can be found that the mutant virus obtained a temperature sensitivity character.

Example 3

Analysis on Productivity Maintenance in a Fertilized Egg

Figure 4:
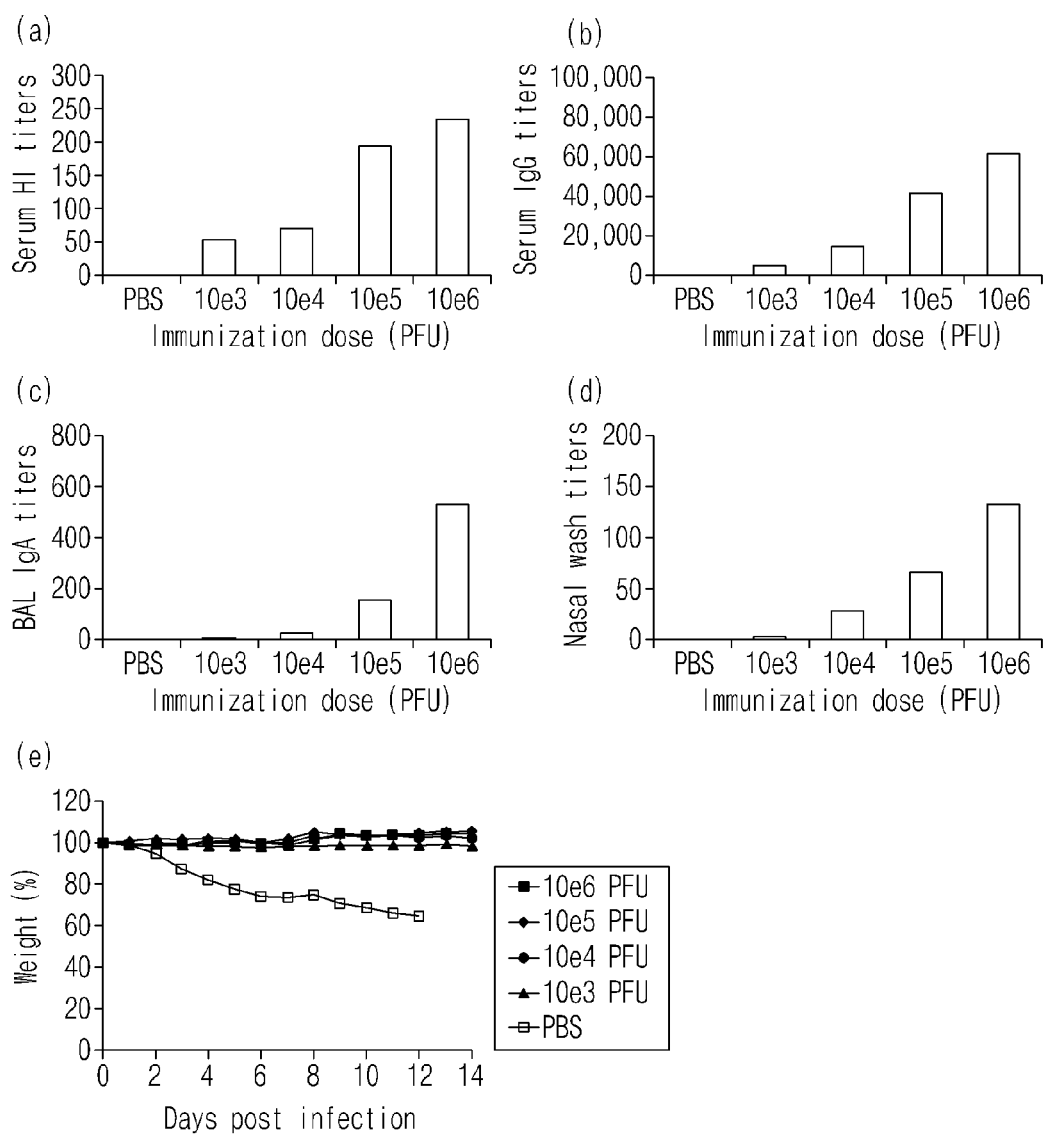
FIG. 4 shows the test result of an antibody response and a protectiveness after DM-C virus vaccination, in a mouse immunized with or non-immunized with DM-C.

The high productivity in a fertilized egg (Korean Poultry TS) as well as the attenuation character provides an advantage in that the cost for production of a live vaccine can be reduced. In order to measure the productivity in a fertilized egg, a virus with 100 PFU (plaque forming unit) was inoculated into a fertilized egg, and cultured for 3 days under various temperature conditions. An allantoic fluid of each fertilized egg was collected and then the amount of virus within the fluid was measured (see FIG. 2b). At 37° C. where a wild type virus is most vigorously grown, the productivity of a mutant virus was reduced about 100 times. On the other hand, when the culture temperature was lowered to 33° C. or 30° C., there was hardly any difference in productivity between the wild type virus and the mutant virus (see FIG. 2b). This result can be easily explained in consideration of the fact that caspase used for the attenuation is an enzyme. In other words, an enzyme showing an optimum activity at 37° C. shows a reduced activity at a low temperature. Likewise, at a low temperature such as 33° C. or 30° C., caspase shows a reduced activity, and thus cleavages of NP and NS1 proteins of an influenza virus in a fertilized egg cannot be smoothly carried out. Especially, a growth reduction of a mutant virus in the MDCK cell line was much greater than in the fertilized egg (see FIG. 2*c*). This result seems to be due to the interspecific difference between the fertilized egg and the MDCK cell line. In other words, it is expected that a series of responses on influenza virus infection in a chorioallantoic membrane (CAM) tissue (where propagation of the influenza virus mainly occurs) in the fertilized egg are different from those occurring in the MDCK cell line (mammalian). Especially, in an apoptosis process, a difference of caspase activation in qualitative and quantitative views allows the productivity of a mutant virus in the fertilized egg to be not reduced compared to a wild type virus. As a result, the DM-C virus having two cleavage sites showed a high growth of $10^8$ PFU/ml (plaque forming units/ml) or more at 33° C. This allows the mass production system using a fertilized egg, as it is, to be utilized.

Example 4

Analysis of Attenuation Characteristic of a Mouse Model

In order to determine the safety as a live vaccine candidate in an animal model, toxicity of a mouse model was tested. A BABL/c female mouse (aged 6 weeks) (from Orientbio) was anesthetized with ketamine, and nasally administered with virus (50 ul). For the mice, a change in the weight and the death rate were measured daily. The toxicity tests on a wild type virus, mutant viruses, and a DM-C:H5N1 reassortant virus were carried out by using 6 mice in each group. The mice were infected with the mutant virus ($10^3$~$10^6$ PFU), while as a control group, the wild type virus ($10^4$ PFU) was inoculated (see FIGS. 3*a* to 3*d*). In the control group, mice showed a rapid weight reduction and then were subsequently all dead on the $7^{th}$ day from the infection (see FIG. 3*a*). Meanwhile, in all mice inoculated with the mutant viruses, the virus toxicity was reduced. When the NP-C virus ($10^3$ PFU) and the NS1-C virus ($10^4$ PFU) were inoculated, there was no reduction in the weight of mice. However, at high concentrations of $10^5$ and $10^6$ PFU (NP-C virus and NS1-C virus, respectively), slight toxicity was shown (see FIGS. 3*b* and 3*c*). Like the test result of propagation capability in the MDCK cell line (see FIG. 2*a*), the toxicity of the DM-C virus was reduced compared to each single mutant virus. In the group inoculated at $10^3$ and $10^4$ PFU, weight reduction was not shown at all, and even at high concentrations of $10^5$ and $10^6$ PFU, a weight reduction of only less than 10% was observed (see FIG. 3*d*). In order to quantify the attenuation of the DM-C virus, virus propagation in the lung and the upper airway of an infected mouse was observed. In order to measure the propagation extent of the DM-C virus in the lung and the upper airway fluid of the mouse, the lungs and the upper airway fluids of 4 mice in each group were collected on the $1^{st}$, $3^{rd}$, $5^{th}$, $7^{th}$ and $10^{th}$ days from the infection. In the mouse infected with the wild type virus ($10^3$ PFU), virus propagation increased immediately after the infection, and within 7 days, a considerable amount of virus was continuously propagated in the lung and the upper airway. Meanwhile, after the infection of the DM-C virus at high concentrations of $10^5$ and $10^6$ PFU, on the $1^{st}$ day, virus propagation was already reduced in the lung (see the left side of FIG. 3*f*), and on the $7^{th}$ day, the virus propagation was reduced up to less than the limit of determination (see FIG. 3*e*). Especially, in the upper airway, from $1^{st}$ day to $10^{th}$ day, no virus was detected (see the right side of FIG. 3*f*). From this result, it can be found that the propagation capability and the toxicity of the DM-C virus were significantly reduced in an animal model as well as a cell line.

Example 5

Analysis of Genetic Stability

Since a gene of an influenza virus is RNA, a mutation may frequently occur during virus propagation. During a subculture process in a production system of a DM-C virus, in order to test the genetic stability of a caspase recognition site, the virus was subjected to subculture ten times in a fertilized egg and an MDCK cell line, and then it was found that the base sequence of the caspase recognition site was not changed. In order to measure the genetic stability of the DM-C virus, the virus was subjected to subculture ten times in a fertilized egg and an MDCK cell line. During a subculture process in a fertilized egg, 10 fertilized eggs were inoculated with a virus (100 PFU), and after 3 day-culture, an allantoic fluid was collected. Then, chicken red blood cells were used to carry out HA assay. From among these, a sample with the highest titer was selected, subjected to measurement of a virus titer through plaque assay in the MDCK cell line, and was used for the following subculture. For subculture using the MDCK cell line, the MDCK cell line was infected with the virus ($10^3$ PFU) obtained from the previous subculture. After culture at 37° C. for 48 hours, the amount of virus within the supernatant was measured through plaque assay. From the virus obtained after subcultures 10 times in the fertilized egg and the MDCK cell line, the RNA was extracted, and then sequencing of NP and NS genes was carried out so as to determine if a mutation had occurred.

Example 6

Test on Antibody Induction and Protectiveness

After 3 weeks from DM-C virus infection, from a serum of a mouse, the amounts of IgG antibody and hemagglutinin inhibition (HI) antibody were measured and from the nasal wash and the lower respiratory tract (BALF), the amount of secretory antibody IgA was measured. The amount of the antibody was expressed as an inverse number of a dilution multiple, in which by the dilution multiple, an O.D value measured at 450 nm through ELISA assay is 0.1 or more. As the amount of infection was increased, the amounts of the antibodies were increased (see FIGS. 4*a* to 4*d*). From the non-infected mice used as a control group, no antibody response was detected. In order to test the protectiveness of infection, after 4 weeks from vaccine inoculation, 10 $LD_{50}$ A/PR/8/34 or A/Aquatic bird/Korea/W81/2005 (ma81) virus (Song, M.-S. et al., The Polymerase Acidic Protein Gene of Influenza A Virus Contributes to Pathogenicity in a Mouse Model. *J. Virol.* 83, 12325-12335 (2009)) was nasally administered. In order to test the protectiveness, after 4 weeks from vaccination, a wild type virus of $10LD_{50}$ was infected. As a result, non-vaccinated mice underwent rapid weight reduction and subsequently all died. Meanwhile, in vaccinated mice, even in mice vaccinated with the lowest concentration of $10^3$ PFU, no infection signs such as weight reduction were observed at all. From this result, it can be found that vaccination using a DM-C virus induced a powerful immune response (see FIG. 4e).

Example 7

Possibility as Attenuated Live Vaccine Parent Strain

Figure 5:
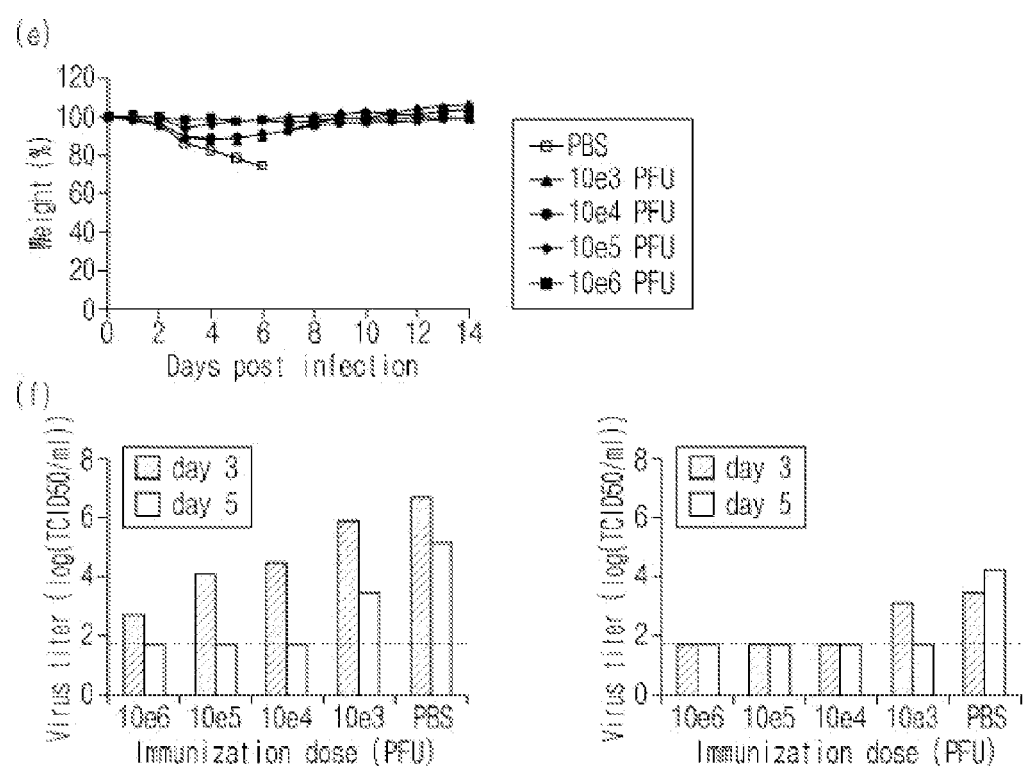

Possibility as a live vaccine parent strain was tested. For this, a 6:2 DM-C:H5N1 reassortant virus was prepared by combining antigen genes HA and NA of A/Indonesia/5/2005 (H5N1) virus with 6 genes of DM-C virus. The propagation speed of the reassortant virus in an MDCK cell line was similar to that of DM-C virus (see FIG. 5a). Also, even in mice infected with a high concentration of $10^3$~$10^6$ PFU, no toxicity was observed. From this result, it can be found that a recombinant virus also obtained an attenuation character by the gene transferred from the DM-C virus (see FIG. 5b). Also, from the capability of inducing a considerable amount of serum IgG antibody and anti-hemagglutinin antibody, it was found that in spite of the high attenuation, the reassortant virus has a high immunogenicity (see FIGS. 5c and 5d). After 4 weeks from vaccination of mice by the reassortant virus, the mice were infected with A/Aquatic bird/Korea/W81/05 (ma81) (H5N2) virus (Song, M.-S. et al., The Polymerase Acidic Protein Gene of Influenza A Virus Contributes to Pathogenicity in a Mouse Model. *J. Virol.* 83, 12325-12335 (2009)) at a concentration of 10 $LD_{50}$, and then their protectiveness was tested. The control group mice administered with PBS were all dead on the $7^{th}$ day, while all of vaccinated mice survived (see FIG. 5e). Even the lowest amount ($10^3$ PFU) of inoculated vaccine resulted in a perfect protectiveness. From this result, it can be found that although the types of a vaccine strain (H5N1) and an infection strain (H5N2) do not completely correspond to each other, a high cross-protectiveness can be achieved. From mice inoculated with vaccine including DM-C:H5N1 reassortant virus, a removal speed of infection virus was measured. For this, 4 mice in each group, after 4 weeks from vaccine inoculation, were infected with 10 $LD_{50}$ A/Aquatic bird/Korea/W81/05 (ma81) virus. In order to precisely determine the propagation and the removal efficiency of infection virus in vaccinated mice, on the $3^{rd}$, $5^{th}$, and $7^{th}$ days from infection, the lung and the upper airway fluid of mice were collected, and the amount of infection virus was measured in an MDCK cell line through TCID50 method (see FIG. 5f).

For 3 days after infection, from the lungs of mice in all groups, infection virus was observed. Meanwhile, from the upper airway fluid, virus was observed in only a group vaccinated with $10^3$ PFU while in other groups vaccinated with greater than $10^3$ PFU, no virus was observed (see FIG. 5f). On the $5^{th}$ day from infection, in the lung, virus was detected only in a $10^3$ PFU-vaccinated group, while in the upper airway fluid, no virus was detected in all groups (see FIG. 5f). On the $7^{th}$ day from infection, in the lung and the upper airway of mice in vaccinated groups, no infection virus was detected at all. In other words, complete virus removal was carried out.

Although several exemplary embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A reassortant influenza virus comprising genes encoding PA, PB1, PB2, NP (nucleocapsid protein), M (matrix protein) and NS1 (nonstructural protein 1), and genes encoding HA (hemagglutinin) and NA (neuraminidase);
wherein amino acids 431 to 434 of NP having the sequence of SEQ ID NO: 4 or amino acids 101 to 104 of NS1 having the sequence of SEQ ID NO: 7 is substituted with a caspase recognition sequence selected from the group consisting of DEVD, AEVD, IETD, WEHD, and YVAD (SEQ ID NO: 11 to SEQ ID NO: 15, respectively).

2. The reassortant influenza virus as claimed in claim 1, wherein the amino acid sequence of the caspase recognition sequence is DEVD (SEQ ID NO: 11).

3. The reassortant influenza virus as claimed in claim 1, wherein the influenza virus is an A-type influenza virus.

4. An attenuated vaccine composition comprising the reassortant influenza virus as claimed in any one of claims 1, 2, or 3.

* * * * *